United States Patent [19]
Davis

[11] Patent Number: 5,366,506
[45] Date of Patent: Nov. 22, 1994

[54] PROXIMITY INTRAURETHRAL VALVE USING PERMANENT MAGNET CHECK

[76] Inventor: Phillip J. Davis, 521 Hahaione Street, #12K, Honolulu, Hi. 96825

[21] Appl. No.: 42,689

[22] Filed: Apr. 5, 1993

[51] Int. Cl.⁵ .......................... A61F 2/04; A61F 2/24; A61F 2/00; A61F 2/02
[52] U.S. Cl. ........................................ 623/12; 623/2; 623/14; 600/29; 600/30
[58] Field of Search ...................... 600/29–31; 604/247, 249; 623/1, 2, 11, 12, 14, 66

[56] References Cited

U.S. PATENT DOCUMENTS

| | | |
|---|---|---|
| 3,642,004 | 2/1972 | Osthagen et al. .................... 604/249 |
| 3,731,670 | 5/1973 | Loe ........................................ 600/30 |
| 3,812,841 | 5/1974 | Issacson . |
| 3,854,469 | 12/1974 | Giori et al. ......................... 623/66 X |
| 3,939,821 | 2/1976 | Roth ....................................... 600/30 |
| 3,952,726 | 4/1976 | Hennig et al. ........................ 600/30 |
| 4,024,855 | 5/1977 | Bucalo .................................. 600/30 |
| 4,154,226 | 5/1979 | Hennig et al. ........................ 600/30 |
| 4,210,132 | 7/1980 | Perlin .................................... 600/30 |
| 4,258,705 | 3/1981 | Sorensen et al. ..................... 600/30 |
| 4,721,095 | 1/1988 | Rey et al. ........................... 623/12 X |
| 4,828,544 | 5/1989 | Lane et al. .......................... 623/1 X |
| 4,904,256 | 2/1990 | Yamaguchi ........................... 623/14 |
| 4,961,725 | 10/1990 | Rey et al. .......................... 623/12 X |
| 4,994,019 | 2/1991 | Fernandez et al. ............... 623/14 X |
| 4,994,020 | 2/1991 | Polyak .............................. 623/14 X |
| 5,004,454 | 4/1991 | Beyar et al. . |
| 5,019,102 | 5/1991 | Hoene ................................. 623/2 X |
| 5,030,199 | 7/1991 | Barwick et al. ..................... 600/29 |
| 5,041,092 | 8/1991 | Barwick ............................ 600/29 X |
| 5,112,306 | 5/1992 | Burton et al. ................... 604/247 X |
| 5,135,538 | 8/1992 | Pawlak et al. ......................... 623/2 |
| 5,140,999 | 8/1992 | Ardito . |
| 5,234,409 | 8/1993 | Goldberg et al. .............. 604/249 X |

FOREIGN PATENT DOCUMENTS

| | | | |
|---|---|---|---|
| 2754807 | 6/1979 | Germany ................... 623/14 |
| 1296128 | 3/1987 | U.S.S.R. .................. 600/29 |

*Primary Examiner*—David Isabella
*Assistant Examiner*—Elizabeth M. Burke
*Attorney, Agent, or Firm*—Harpman & Harpman

[57] ABSTRACT

An urethral magnet valve for insertion into the urethra of a person suffering from incontinence defines a binary duct relief valve comprising a nonferromagnetic tubular housing containing a valve member of a permanent magnet encapsulated within a nonmagnetic material, enabled on a valve seat of high magnetic permeability ferromagnetic nature, by a magnetic attraction therebetween. Retaining flanges integral with the housing prevent escape of the valve element when valve is open. A manually held external positioned permanent switching magnet induces magnetic torque and attraction on the valve element causing it to rotate within the tubular housing lifting same from the valve seat opening the passageway therethrough and through urethra.

18 Claims, 4 Drawing Sheets

PROXIMITY INTRAURETHRAL VALVE USING PERMANENT MAGNET CHECK

BACKGROUND OF THE INVENTION

1. Technical Field

This device relates to intraurethral magnetic valves that are used to provide a valving means for individuals suffering from an inability to control their bladder functions by substituting a mechanical magnetic actuated valve to control the flow of urine.

2. Description of Prior Art

Prior art devices of this type have relied on a wide variety of different magnetic valve configurations that attempt to control the fluid flow from the bladder. Examples of same can be defined and divided into two basic designs; 1) ferromagnetic spheres or slugs which seal an aperture by attraction to one or more fixedly located permanent magnets within a valve housing and are drawn away from the aperture by a strong permanent magnet or electromagnetic field induced by a hand held magnet located outside the valve housing, see for example U.S. Pat. Nos. 3,731,670 and 5,004,454.

The second design group is characterized by permanent magnets bonded to nonmagnetic valve checks which are drawn to seal an aperture by attraction to a ferromagnetic element comprising all or part of the aperture or are resiliently held in closed position on the aperture by a spring. These checks are drawn in a straight linear motion away from the apertured valve seat by a hand held magnet outside the valve housing, see for example U.S. Pat. Nos. 3,812,841 and 5,140,999.

In U.S. Pat. No. 3,731,670 a corporeal fluid control using binary magnetic duct valve is disclosed wherein a mounting tube has two spaced magnets with a steel ball valve element therebetween. The ball valve element is selectively attracted to each of the magnets defining an open or closed state depending on which magnet the ball is engaged. The ball is reciprocated within the structure by an external magnetic force.

U.S. Pat. No. 5,004,454 is directed to an auxiliary intraurethral magnetic valve wherein a plastic tube defines the valve body and a valve seat. A valve element of a ferromagnetic material is held in sealing relation against the valve seat by a spring associated therewith. The valve is opened by imposing a magnetic force on the valve element drawing same away from the seat and stretching the spring.

The devices defined by the first set of prior art valves suffer from an intrinsic difficulty in balancing the magnetic force needed for adequate sealing with the need for reasonable operational range of the activation magnet.

Since magnetic forces are highly nonlinear, decreasing very rapidly with distance from the magnetic poles; when a ferromagnetic ball or slug is held against an aperture by a permanent magnet element the respective switching magnet must be either very large or very close to induce the required force. The slug checks that are drawn to the side of the housing encounter high sidewall friction forces which are induced increasingly as the angle between the housing center line and the line of approach of the switching magnet increases.

In U.S. Pat. No. 3,812,841 a urethra magnetic valve structure can be seen in which a valve element is positioned on a movable magnetic core cylinder. The valve element is held in closed position by an attached spring. Inducing a high electromagnetic force from outside the body will move the magnetic core cylinder and valve element attached thereto opening the valve.

In U.S. Pat. No. 3,812,841, the valve check movement is constrained by the housing to a straight line which necessitates that unless the switching magnet approaches with its axis directly aligned on the center line the force will draw the check against the sidewall imparting torque induced friction decreasing the effectiveness and movement of the check within the valve housing.

U.S. Pat. No. 5,140,999 is directed to an implantable valve structure in which the valve element extends well within the bladder for increased lateral operational movement. The valve element has a compression spring engaging same in a closed or checked position. Upon inducement of an outside magnetic force the magnetizeable member on the free end of the valve element within the bladder is displaced to the side moving the respective valve element off its valve seat opening the valve. No accommodation is made for bladder neck movements or changes in bladder inflation which may cause unwanted movements of the free end of the valve element.

The present invention overcomes the drawbacks of small working distance and sidewall friction by utilizing as operating forces the torque induced between the dipoles of the valve element and the switching magnet and the direct magnetic attraction between same. In the preferred embodiment the valve element pivots freely within the confines of the housing to align its magnetic poles with respective poles of the switching magnet used. This results in a large ratio of switching magnet working distance to housing diameter, virtual omnidirectionality for the switching magnet approach and nonpolarity of the switching magnet orientation.

In an alternate form of the invention, the valve element is hinged so that torque induced by the switching magnet and direct magnetic attraction will cause it to rotate in an arc about a pivot point within the housing aligning its magnetic poles with poles of the switching magnet. The same benefits apply to the alternate form of the invention as hereinbefore described with the preferred embodiment.

SUMMARY OF THE INVENTION

An intraurethral magnetic valve having an incapsulated ferromagnetic valve element within a nonferromagnetic housing. The valve element is magnetically retained in closed check position against a valve seat restricting the flow of fluid through the valve. An outside switching magnet is used to impart magnetic torque to the valve element displacing it from the valve seat opening the valve for fluid flow.

DESCRIPTION OF THE PREFERRED EMBODIMENT

Figure 1:
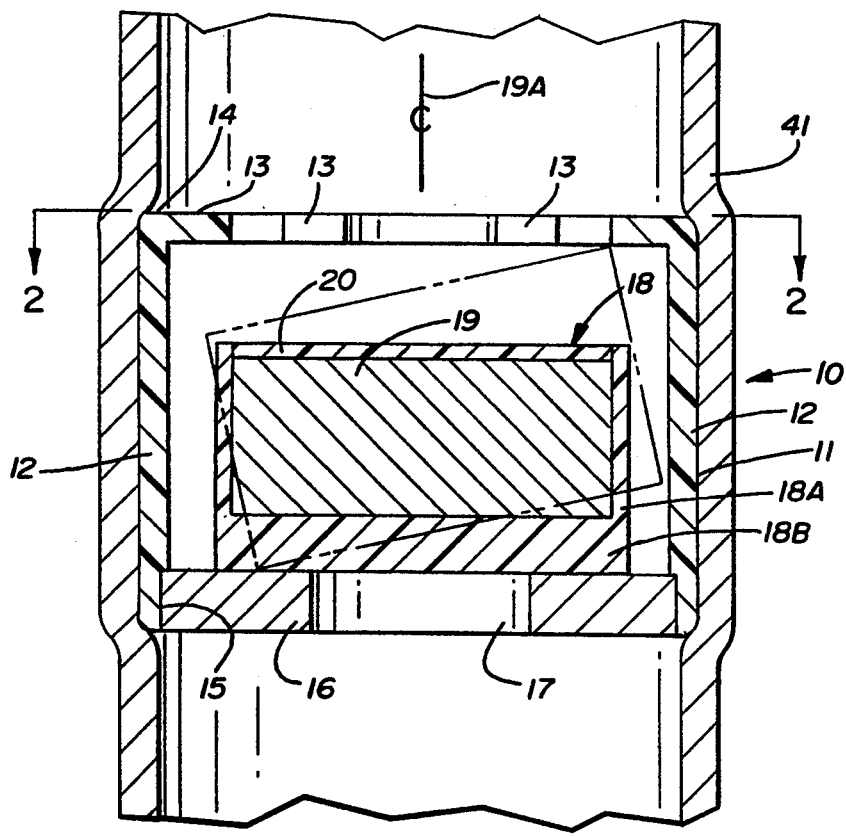
FIG. 1 is a sectional view taken through the valve embodying the novel features of the present invention within a placement catheter.
Figure 2:
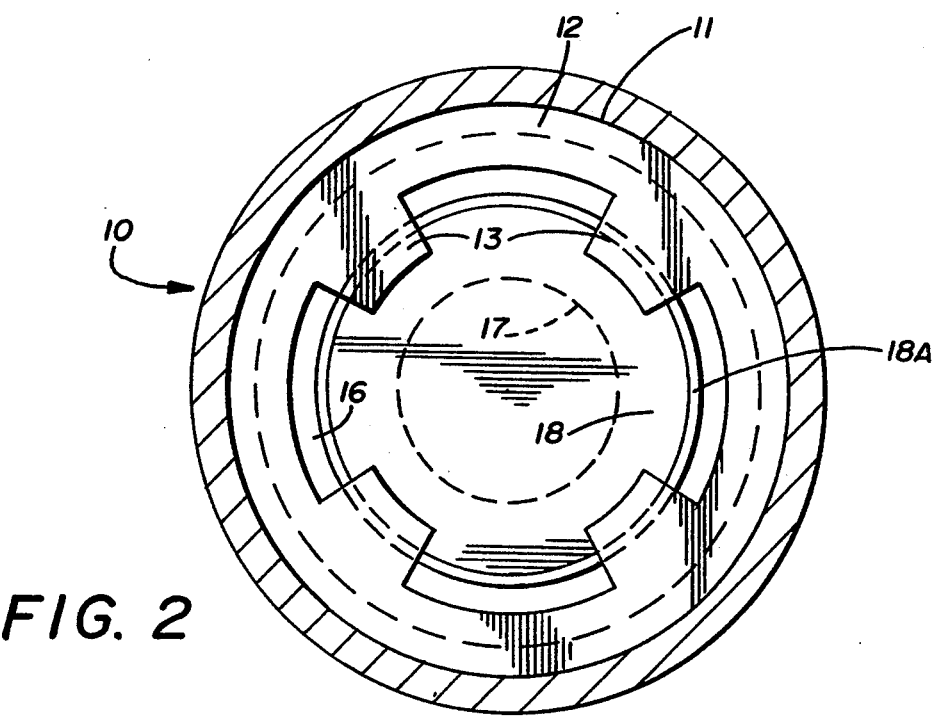
FIG. 2 is a section on lines 2—2 of FIG. 1.
Figure 3:
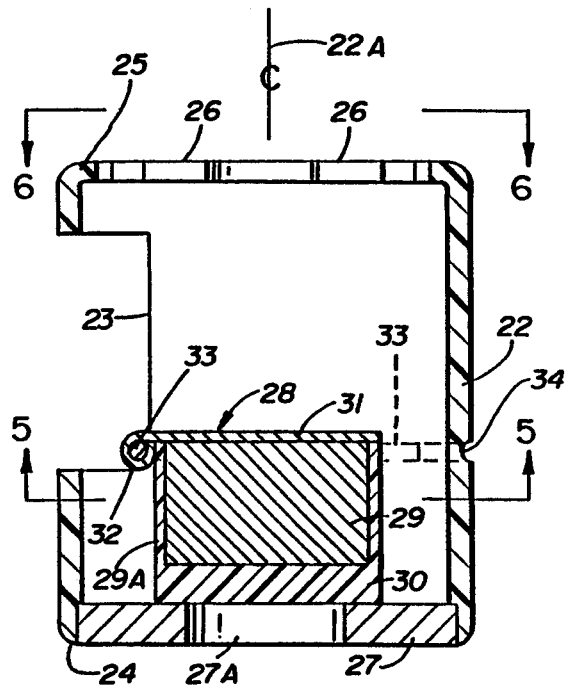
FIG. 3 is a sectional view of an alternate form of the valve embodying the novel features of the present invention in closed position.

Referring to FIGS. 1 and 2 of the drawings, a valve assembly 10 can be seen comprising a cylindrical nonmagnetic housing 11 having a continuous side wall 12. A plurality of annularly spaced retaining flanges 13 extend inwardly from a perimeter edge 14 of said cylindrical housing 11 defining said sidewall 12. A recessed area 15 in said sidewall 12 extends inwardly from its free end defining a mounting surface for registration with a ferromagnetic valve seat 16. The valve seat 16 has a cylindrical aperture at 17 concentric within said cylindrical housing 11. A valve element 18 is comprised of a cylindrical magnet 19 encapsulated within a generally U-shaped nonmagnetic capsule 18A of biocompatible material having a thicker base portion 18B adjacent the valve seat 16 and an oppositely disposed closer 20 adhesively fixed to the magnet 19.

The valve element 18 is normally attracted to the ferromagnetic valve seat 16 for sealing registration therewith occluding the cylindrical aperture at 17 closing the valve 10. The magnet 19 is magnetized along its central line axis, as is well known in the art.

The flanges 13 may also be used as engagement points for gripping and positioning the valve assembly 10 within the body lumen or placement catheter as will be described in greater detail later.

It is critical that the magnet 19 have high coercive force and high residual flux density to achieve the proper durability and sealing ability.

Referring to FIG. 1 of the drawings, the valve assembly 10 is shown in closed position with the valve element 18 shown in broken lines indicating the free range of travel required during operation and thus the relative clearance of the valve element 18 within the housing 11 when open.

Figure 8:
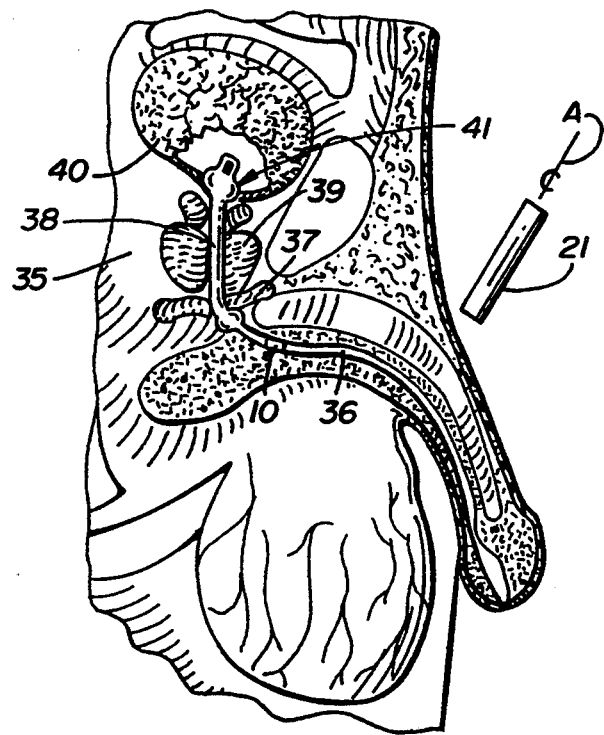
FIG. 8 is a sectional view of a portion of a body of a human showing the device of the present invention implanted for controlling flow through the urethra.

This valve "open" position occurs upon activation of the valve element 18 by a switching magnet 21, seen in FIG. 8 of the drawings. The switching magnet 21 is of a generally bar configuration in this example having been magnetized along its longitudinal center line axis A. When the switching magnet 21 is brought into close proximity to the valve element 18 as indicated with their respective magnetic center lines in a non-axial alignment, magnetic torque is induced on the valve element 18. The misalignment of the respective magnetic fields of the switching magnet 21 and the magnet 19 within the valve element 18 induces the valve element 18's rotation and repositioning within the housing 11 shown in broken lines in FIG. 1 of the drawings, thus opening the valve assembly 10 for passage of fluid. The valve element 18 must be of a sufficient size to prevent excess rotation that would and could lead to a potential to jam or impinge against the inner surface of the housing 11 thus preventing reseating of the valve element 18 in the aperture occluding position by the limited magnetic attraction available.

The retaining flanges 13 limit the valve element 18 relative movement within the housing so that the required range of magnetic attraction between the valve element 18 and said valve seat 16 is sufficient to return the valve element 18 to the aperture occluding position upon deactivation i.e. removal of the switching magnet 21 (as shown in solid lines in FIG. 1 of the drawings).

When the switching magnet 21 is not present, as indicated, the hereinbefore valve element 18 is attracted to ferromagnetic valve seat 16 occluding the cylindrical aperture 17 therein.

The valve element 18 also acts as a high pressure relief element, with relief pressure determined by the magnitude of the attraction forces between the valve element 18 and valve seat 16 at the relative separation distance imposed by the nonferromagnetic base portion 18B of the capsule 18A. The axial symmetry of the valve seat 16 and the magnet 19 within the valve element 18 limits magnetic attractive forces that tend to draw the valve element 18 against the inner walls of the housing 11 and thus limits friction between the housing 11 and valve element 18. This symmetry also provides uniform distribution of closure force around cylindrical aperture at 17 in the valve seat 16. Relief pressure may be altered by varying any combination of the nonferromagnetic capsule base 18B thickness, the valve seat 16's mass, the valve seat 16's magnetic permeability, or the magnet 19's mass, its respective magnetic aspect ratio (length to diameter) or its magnetic residual flux density in the valve element 18, and valve seat 16's aperture area at 17.

The switching magnet 21 may be positioned at any angle relative to the valve element 18 and enclosed magnet 19 center line axis indicated at 19A.

Referring now to FIGS. 3-6 of the drawings, an alternate form of the invention can be seen wherein a cylindrical valve housing 22 has a cut through its sidewall at 23 inwardly of its respective ends 24 and 25. Retaining flanges 26 and valve seat 27 apertured at 27A are identical to those described in the primary form of the invention hereinbefore described.

A hinged valve element 28 is of a similar construction as that of said valve element 18 having an encapsulated magnet 29 adhesively bonded within a biocompatible material and a nonferromagnetic capsule 29A characterized by a thicker base portion 30.

The hinge valve element 28 has a mounting plate closure 31 that is secured to the encapsulated magnet 29 opposite said base portion 30. The mounting closure plate 31 extends to form a knuckle 32 configured thereon for pivotal registration of a hinge pin 33 that extends through said knuckle 32 and around the exterior surface of the cylindrical valve housing 22 in a mounting groove 34, best seen in FIGS. 5 and 6 of the drawings. The hinged valve element 28 is normally in closed position indicated in FIG. 3 of the drawings with the magnetic attractive forces of the respective encapsulated magnet 29 reactive to apertured valve seat 27.

Figure 4:
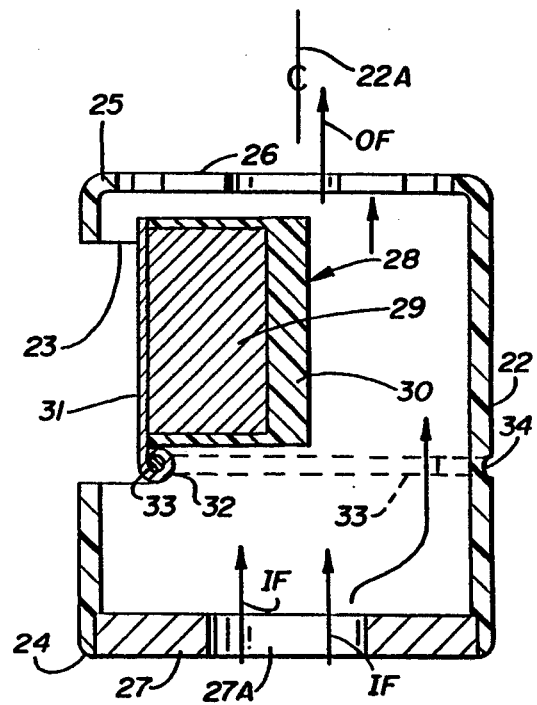
FIG. 4 is a sectional view of the alternate form shown in FIG. 3 in open position.
Figure 5:
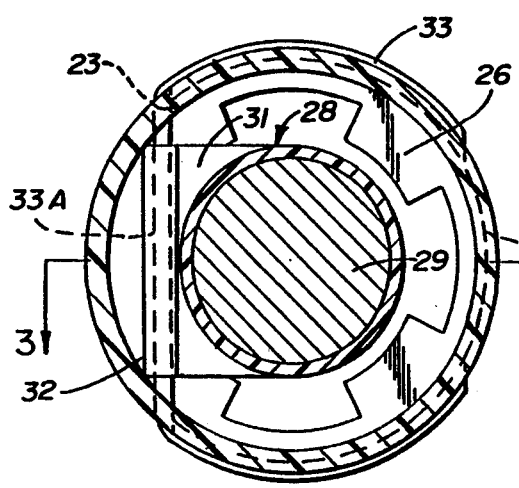
FIG. 5 is a section on lines 5—5 of FIG. 3.
Figure 6:
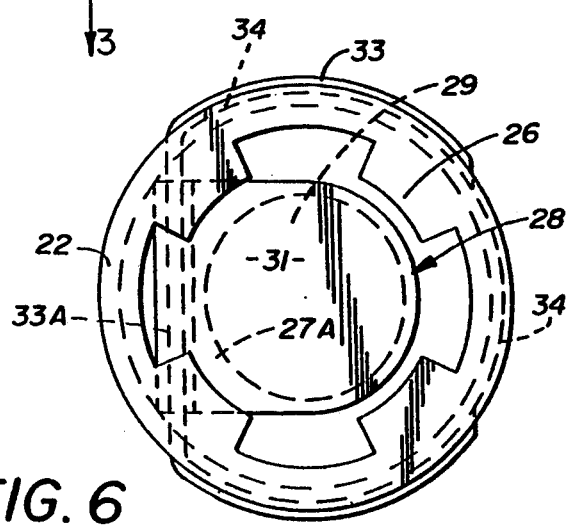
FIG. 6 is a section on lines 6—6 of FIG. 3.

In use, under the magnetic pull from the switching magnet 21, hereinbefore described, the hinged valve element 28 is pivoted to an open non-occluded position as shown in FIG. 4 of the drawings allowing for free flow of fluid through the valve. In this alternate example of the invention when the switching magnet 21 is brought into close proximity to the valve, with its respective center line A in or closely aligned to an activation plane defined by the center line 22A of the valve housing 22 and the perpendicular bisector of the straight portion of the hinge pin 33 at 33A and the switching magnet 21's closest end having appropriate magnetic polarity to the outflow side of the encapsulated magnet 29 indicated by arrows OF in FIG. 4 of the drawings of the encapsulated magnet 29, then two valve open conditions are possible.

The first valve open position being with the switching magnet 21 on the outflow side of the encapsulated magnet 29, the magnetic attraction therebetween overcomes that of said valve seat 27.

The second condition for a valve opening is when the switching magnet 21 is on the inlet flow (indicated by arrows IF) of the encapsulated magnet 29, magnetic repulsion exceeds attraction between encapsulated magnet 29 and the valve seat 27. Additional force tending to open the valve is provided by magnetic torque induced by the valve element 28 and the misalignment of the switching magnet 21 and valve element 28's magnetic fields, hereinbefore described. Thus the switching magnet 21 may be anywhere in the activation plane, but should not approach with its midplane coincident with the midplane of the encapsulated magnet 29 where the effective working distance is least.

In FIG. 8 of the drawings, a partial cross-section through a human abdomen 35 is illustrated to determine the positioning of the valve assembly 10 within the patient. The abdomen 35 contains the bulbous urethra 36, external sphincter 37, prostatic urethra 38, prostate 39 and bladder 40 defined for this discussion.

Figure 7:
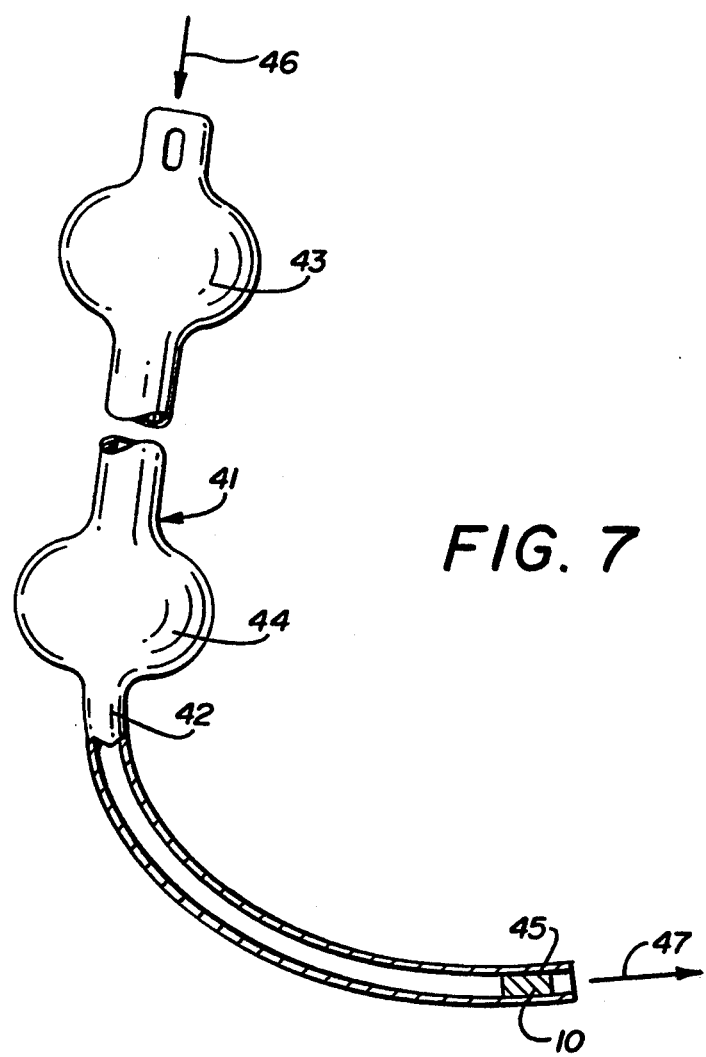
FIG. 7 is a side plan view with portions in sections showing a catheter placement device for the valve embodying the novel features of the invention.

Referring now to FIGS. 7-8 of the drawings, an example of a placement vehicle for the valve assembly 10 can be seen. In this example, chosen for illustration, a modified catheter 41 can be seen having an elongated tubular body member 42 with longitudinally spaced retention bulges 43 and 44 illustrated thereon. A portion of the catheter 41 within the prostatic urethra 38 will be constructed to resist collapse and be held within by the retaining bulge 43 within the bladder 40 and adjacent the external sphincter 37 as illustrated by the bulge 44 extending as near as possible thereto within the bulbous urethra 36.

The valve 10 of the invention is positioned within the catheter 41 adjacent the distal end at 45. The catheter 41 is designed to be easily placed and removed much like the intermittent catheterization well known to those skilled in the art.

The valve assembly 10 within the catheter 41 is flow oriented so that the respective valve seats 16 and 27 illustrated are adjacent the upstream flow indicated by the respective inflow arrows IF shown in FIG. 4 of the drawings.

Figure 9:
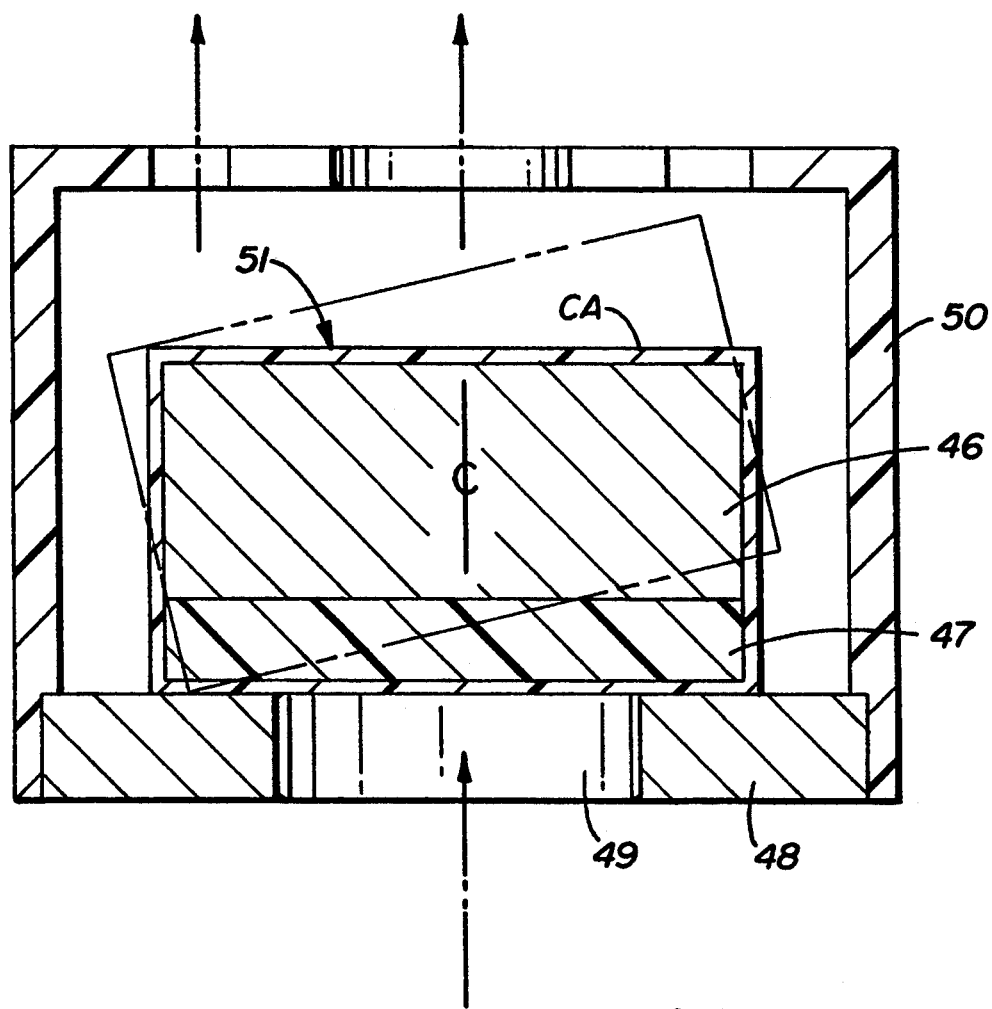
FIG. 9 is a sectional view of an alternate form of the invention showing an encapsulated magnet.

Referring now to FIG. 9 of the drawings, an alternate form of the invention is illustrated wherein a cylindrical housing 50 has a valve element 51 within, said valve element 51 is defined by a permanent magnet 46 encapsulated within a coating or plating of biocompatible materials CA bonded to a nonferromagnetic cylindrical pad 47 by adhesive fixation. The pad 47 would be engageable in sealing relation against a valve seat 48 apertured at 49 corresponding to the hereinbefore described valve seats 16 and 27 shown in respective valve element configurations 18 and 28.

It will be apparent to those skilled in the art that the valve assembly 10 being disclosed and described can be used in other environments not exclusive to the human body where reliable self-contained remotely actuated valves are required.

It will be apparent to those skilled in the art that various changes and modifications may be made therein without departing from the spirit of the invention, therefore I claim:

I claim:

1. An intraurethral magnetic valve for insertion into the urethra of a person's body comprising in combination a tubular housing, a valve element within said housing, and a valve seat sealingly engaged by said valve element, said tubular housing is non-magnetic having an internal recessed area adjacent one end thereof, a plurality of spaced fingers extending inwardly from said tubular housing in spaced relation to said recessed area, said valve seat in annular registration with said recessed area in said tubular housing, said valve element comprising an encapsulated permanent magnet magnetized along a center line axis, a nonferromagnetic means for encapsulation spacing said permanent magnet, means for spacing said permanent magnet in respect to said valve seat, said element being normally attracted to said valve seat occluding and sealing same, means for opening said valve comprising a source of magnetic attraction in spaced relation to said person's body, said magnetic attraction selectively imposes a magnetic field on said valve element pivoting same away from said sealing relation with said valve seat, and means for inserting said magnetic valve assembly within the urethra of said person's body.

2. The intraurethral magnetic valve of claim 1 wherein said permanent magnet, and said means for encapsulating and spacing said permanent magnet in relation to said valve seat are cylindrical.

3. The intraurethral magnetic valve of claim 1 wherein said means for spacing said magnetic valve element in respect to said valve seat comprises a nonferromagnetic area secured to said permanent magnet having a planar flattened surface to impart a fluid seal between said nonferromagnetic area and said valve seat.

4. The intraurethral magnetic valve of claim 1 wherein said means for opening said magnetic valve comprises a permanent switching magnet, said switching magnet magnetized along a center line axis.

5. The intraurethral magnetic valve of claim 1 wherein said means for inserting said magnetic valve within the urethra of said person's body comprises a contoured placement catheter having an elongated tubular body member, areas of longitudinally spaced retention bulges for resiliently positioning and securing said catheter within said urethra.

6. A intraurethral magnetic valve for insertion into the urethra of a person comprising in combination a tubular housing, a hinge valve element within said housing, a valve seat sealingly engaged by said valve element, said tubular housing is non-magnetic having an internal recessed area adjacent an upstream end thereof, said valve seat positioned for annular sealing registration with said recessed area, a plurality of annularly spaced flanges extending inwardly from said tubular housing and spaced in opposing relation to said valve seat, said valve element comprising an enclosed permanent magnet magnetized along a center line axis, a mounting hinge integral to said enclosed magnet and a pivot pin engaging said hinge valve element within said tubular housing, means for spacing said permanent magnet in relation to said valve seat, means for opening said valve by a source of magnetic attraction in spaced relation to said person, and means for securing said magnetic valve within the urethra of said person.

7. The intraurethral magnetic valve for insertion into the urethra of a person of claim 6 wherein said means for spacing said permanent magnet in said valve element in relation to said valve seat comprises a nonferromagnetic area secured to said permanent magnet to impart a fluid seal between said nonferromagnetic area and said valve seat.

8. The intraurethral magnetic valve of claim 6 wherein said means for opening said magnetic valve by a source of magnetic attraction comprises a permanent switching magnet magnetized along a center line axis.

9. The intraurethral magnetic valve of claim 6 wherein said means for securing said magnetic valve within the urethra of said person's body comprises a contoured placement catheter having an elongated tubular body member having areas of longitudinally spaced retention bulges for positioning and securing said contoured placement catheter within person in communication with the bladder and the urethra.

10. A magnetic valve comprising in combination a tubular housing, a valve element within said housing, and a valve seat adjacent one end thereof, said valve seat sealingly engaged by said valve element, said tubular housing is non-magnetic, a plurality of projections extending inwardly from said tubular housing in spaced relation to said valve seat, and said valve seat in annular registration with said tubular housing, said valve element comprising an encapsulated permanent magnet magnetized along a center line axis, a nonferromagnetic means for encapsulation of said permanent magnet, means for spacing said permanent magnet in respect to said valve seat, said valve element being normally attracted to said valve seat occluding and sealing same, means for opening said magnetic valve by a source of magnetic attraction positioned in spaced relation thereto, said source of said magnetic attractive selectively imposes a magnetic field on said valve element pivoting same away from said valve seat, opening a passage through said magnetic valve.

11. The magnetic valve of claim 10 wherein said encapsulated permanent magnet and said valve seat are cylindrical.

12. The magnetic valve of claim 10 wherein said means for spacing said magnetic valve element in respect to said valve seat comprises a nonferromagnetic area secured to said permanent magnet, said nonferromagnetic area having a planar flattened surface to impart a fluid seal between said magnet valve element and said valve seat.

13. The magnetic valve of claim 10 wherein said means for opening said magnetic valve by a source of magnetic attraction comprises a permanent switching magnet magnetized along a center line axis.

14. A magnetic valve comprising in combination a tubular housing, a hinge valve element within said housing, a valve seat engaged by said valve element, said tubular housing is non-magnetic, said valve seat positioned for annular sealing registration within said tubular housing, means for selectively retaining said valve element within said tubular housing, said valve element comprises an encapsulated permanent magnet magnetized along a center line axis, a mounting hinge integral to said encapsulated permanent magnet and a pivot pin engaging said mounting hinge and said tubular housing, means for spacing said permanent magnet in relation to said valve seat, means for opening said valve by a source of magnetic attraction located in spaced relation to said tubular housing.

15. The magnetic valve of claim 14 wherein said means for selectively retaining said valve element within said tubular housing comprises flanges extending inwardly from said tubular housing and spaced in relation to said valve seat.

16. The magnetic valve of claim 14 wherein said means for spacing said permanent magnet in relation to said valve seat comprises a nonferromagnetic area secured to said permanent magnet to impart a fluid seal between said nonferromagnetic area and said valve seat.

17. The magnetic valve of claim 14 wherein said means for opening said magnetic valve by a source of magnetic attraction comprises a permanent switching magnet magnetized along a center line axis.

18. The magnetic valve of claim 14 wherein said encapsulated magnet comprises a biocompatible coating and plating and said means for spacing said permanent magnet in respect to said valve seat comprises a nonferromagnetic pad secured to said permanent magnet to impart a fluid seal between said magnet and said valve seat.

* * * * *